United States Patent

Thornburg et al.

[11] Patent Number: 5,620,321
[45] Date of Patent: Apr. 15, 1997

[54] ORTHODONTIC APPLIANCE

[75] Inventors: David W. Thornburg, LaPorte; Philip S. Horvath, New Carlisle, both of Ind.

[73] Assignee: TP Orthodontics, Inc., LaPorte, Ind.

[21] Appl. No.: 444,232

[22] Filed: May 18, 1995

[51] Int. Cl.$^6$ .................................................. A61C 3/00
[52] U.S. Cl. ................................................ 433/19; 433/7
[58] Field of Search ................................. 433/7, 18, 19, 433/21, 22, 24

[56] References Cited

U.S. PATENT DOCUMENTS

| | | | |
|---|---|---|---|
| 473,040 | 4/1892 | Wilder | 433/18 |
| 597,582 | 1/1898 | Knapp | 433/19 |
| 3,618,214 | 11/1971 | Armstrong | 433/19 |
| 3,690,003 | 9/1972 | Gerber | 433/19 |
| 3,798,773 | 3/1974 | Northcutt | 433/19 |
| 4,382,783 | 5/1983 | Rosenberg | 433/19 |
| 4,424,032 | 1/1984 | Howe | 433/19 |
| 4,462,800 | 7/1984 | Jones | 433/19 |
| 4,472,139 | 9/1984 | Rosenberg | 433/19 |
| 4,551,095 | 11/1985 | Mason | 433/19 |
| 4,795,342 | 1/1989 | Jones | 433/19 |
| 5,011,404 | 4/1991 | Losi | 433/19 |
| 5,183,388 | 2/1993 | Kumar | 433/19 |
| 5,328,364 | 7/1994 | Doyle | 433/18 |
| 5,352,116 | 10/1994 | West | 433/19 |
| 5,378,147 | 1/1995 | Mihailowitsch | 433/19 |

*Primary Examiner*—Nicholas D. Lucchesi

[57] ABSTRACT

The telescoping mandibular advancing device is an orthodontic appliance used to promote the forward displacement of the lower jaw. The appliance comprises a pair of telescoping devices that attach on one end to the maxillary arch via a modified ball and socket device and on the other end to the mandibular arch via a modified ball and socket device. The modified ball and socket attachments are specifically designed to simplify installation and adjustment of the appliance. The device is also designed to minimize patient discomfort.

2 Claims, 5 Drawing Sheets section A-A

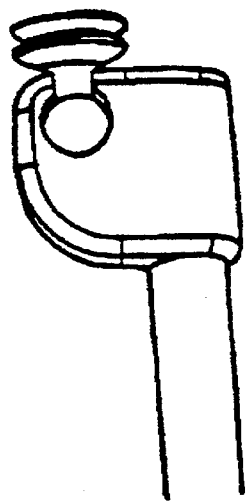
FIG. 13
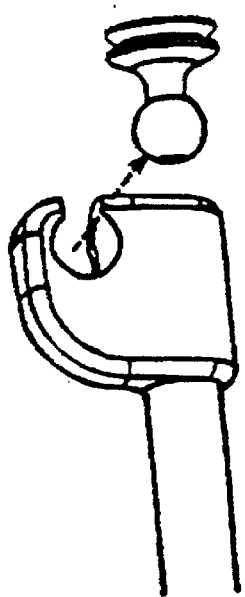
FIG. 12
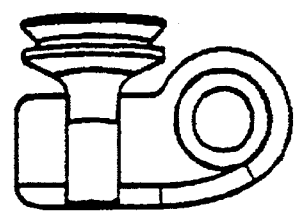
FIG. 16
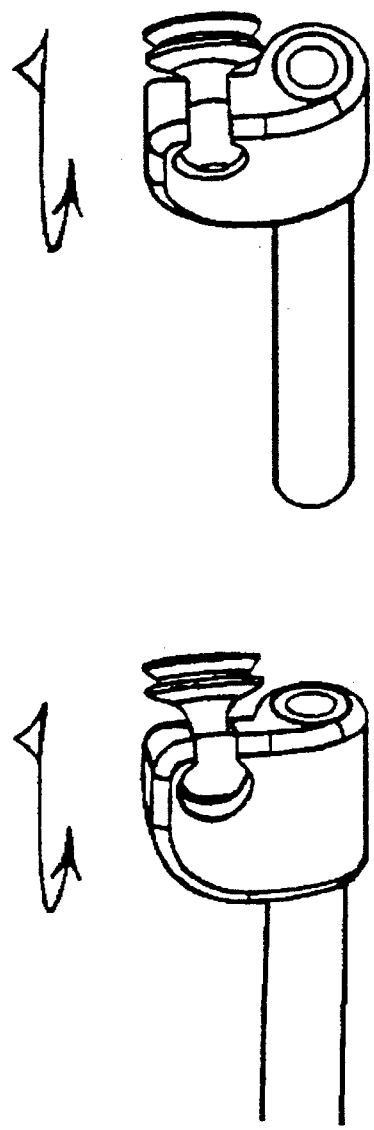
FIG. 15
FIG. 14

5,620,321

ORTHODONTIC APPLIANCE

TECHNICAL FIELD

This device is an orthodontic appliance, more particularly a telescoping mandibular advancing device.

BACKGROUND

A telescoping mandibular advancing device is an appliance used in the orthodontic field to change the relationship between the patient's upper jaw (maxilla) and the lower jaw (mandible). Such therapy is well known to the field of orthodontics and has been disclosed m text books and professional journals for over fifty years. A number of devices to aid in this treatment are readily available. Some are covered by the following U.S. Pat. Nos.: 597,582; 3,618,214; 3,690,003; 3,798,773; 4,382,783; 4,424,032; 4,462,800; 4,472,139; 4,551,095; 5,183,388; 5,352,116; 5,378,147.

SUMMARY OF THE INVENTION

Typical appliances for this treatment consist of a matched pair of force transmission members that are able to supply a force in compression but are unrestricted in tension. These members are applied to an orthodontic anchoring appliance such that one end of each member is connected to the maxillary molars of the patient and the other end of each is anchored to the mandible in the bicuspid region of the dental arch. The attachments at the ends of the force members have a hinge mechanism to allow some freedom of movement of the jaws while still providing the prescribed force for mandibular advancement. A specific version of these devices uses a telescoping rod and sleeve assembly for its force transmission member and is generally known to the field as a Herbst Appliance. A number of variations of the Herbst Appliance are currently available. More background information on the Herbst and other mandibular advancement devices can be found in Larry W. White, *Current Herbst Appliance Therapy*, Journal of Clinical Orthodontics, May 1994.

As pointed out in the White article, there are many problems associated with the installation, adjustment, and use of current Herbst Appliances. These include:

Connection of the hinges is difficult and time consuming, particularly the hinges in the posterior of the mouth which are not readily accessible.

Periodic adjustment of the appliance requires removal of at least one hinge and thus, is difficult and time consuming.

Installation and adjustment often require tools to install and remove which increases the potential for injury to the patient's oral tissues.

Current devices have a history of failure by disconnecting under normal oral forces, or tampering by uncooperative patients. This can result in considerable inconvenience for the patient and doctor, as well as discomfort for the patient.

Current devices often have high, uneven profiles and sharp edges which cause considerable trauma to the patient's oral tissues.

Hinge designs of most current devices unduly impede the lateral movement of the patient's jaws.

It is the intention of this invention to provide an appliance for advancement of the mandible with the following features:

Simplified installation procedures to reduce installation and adjustment time as well as the potential for tissue injury from installation tools.

The buccal (the cheek side of the posterior teeth ) surfaces of the appliance have smooth and even profiles for reduction of irritation and ulceration of oral tissues. A lower surface profile height contributes to patient comfort.

The ball and socket design in conjunction with clearance recesses increase the freedom of lateral movement of the patient's jaws.

Simplified one-piece design of sockets reduces potential for improper fit of assemblies and failure separate parts. The overall reliability of the appliance is improved, reducing both inconvenience to the doctor and risks to the patient.

Appliance advancement can be achieved without disassembly of the mandibular hinge, further reducing appliance adjustment time and potential for oral injury from installation and removable tools.

DESCRIPTION OF THE DRAWINGS

A more complete understanding of the invention may be had by reference to the following detailed description when taken in conjunction with file accompanying drawings where:

(FIGS. 12–16 Sequence of assembly for maxillary hinge)

FIG. 12 Maxillary tube member placed mesial of ball attachment.

FIG. 13 Maxillary tube member shifted distally to engage socket on ball attachment.

FIG. 14 Maxillary tube member in process of being rotated.

FIG. 15 Maxillary tube member in process of being rotated.

FIG. 16 Maxillary tube member in final position with tube along side buccal surface of upper arch.

FIG. 17 Mandibular rod member located distal of the ball attachment.

FIG. 18 Mandibular rod member engaged on ball attachment with pliers positioned to crimp legs of mandibular rod member.

FIG. 19 Split spacer ting in position in pliers and oriented for assembly on mandibular rod member.

FIG. 20 Split spacer ring in final position on mandibular rod member being closed with pliers.

DESCRIPTION OF THE INVENTION

Figure 2:
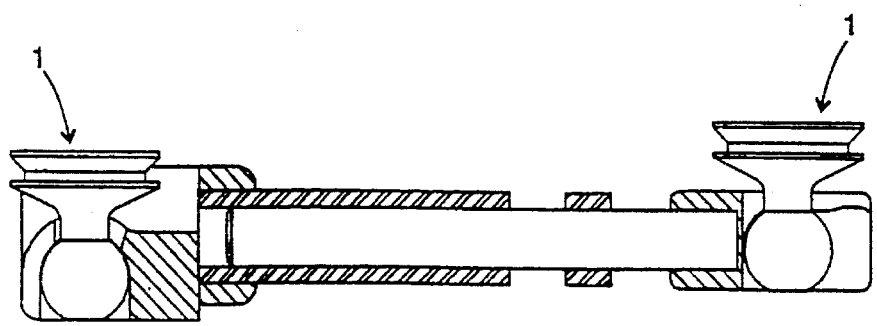
FIG. 2 Sectional view A—A of assembly shown in FIG. 1.
Figure 3:
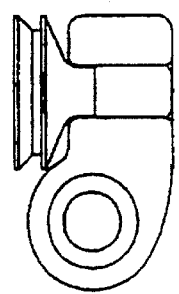
FIG. 3 Distal end view of maxillary tube member.
Figure 4:
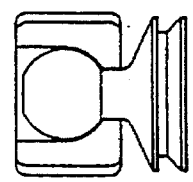
FIG. 4 Mesial end view of mandibular rod member.

This invention comprises a number of components which collectively represent the hardware necessary for the construction of one orthodontic therapy appliance for the treatment of one patient. The telescoping mandibular advancing device comprises: two ball joint attachments; a maxillary tube member; a mandibular rod member; and appliance advancement spacers. A description of the device is as follows:

The ball joint attachments 1 are composed of any non-toxic corrosion resistant material which is suitable for the oral environment such as a 300 series stainless steel or any other material used extensively for orthodontic applications. The ball joint attachments can be manufactured using any of a number of fabrication processes including but not limited to: machining (turning) from bar stock, casting, or sintering. The main features of the ball joint attachments are the spherical ball head 5, and the stem 6, the mounted flange 7, and the retention groove 8.

The ball head 5 of the ball joint attachment performs the traditional function of a ball hinge—transmission of force in a particular direction while allowing freedom of rotation and lateral movement. The stem 6 is a cylindrical member joining the ball head to the mounting flange 7 and is an integral feature for the ball and socket assembly of this invention which will be detailed in later descriptions. The interface between the stem and flange is contoured with a generous radius 9 to eliminate sharp corner stress concentrations. The base of the ball joint hinge is a large flange 7 for the purpose of increasing surface area for the attachment to the dental anchoring appliance. A groove 8 is provided around the circumference of the part just above the mounting flange base. This groove 8 is to provide an undercut for the bonding material of the anchoring appliance, thereby providing a mechanical bond of the base to the appliance.

Figure 9:
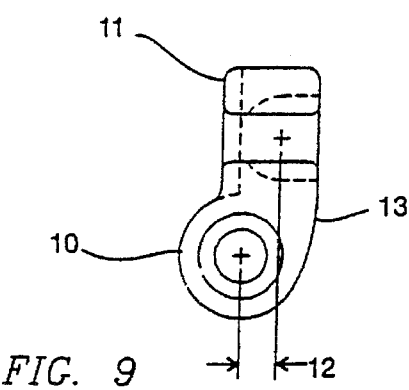
FIG. 9 Detailed distal end view of FIG. 8.
Figure 8:
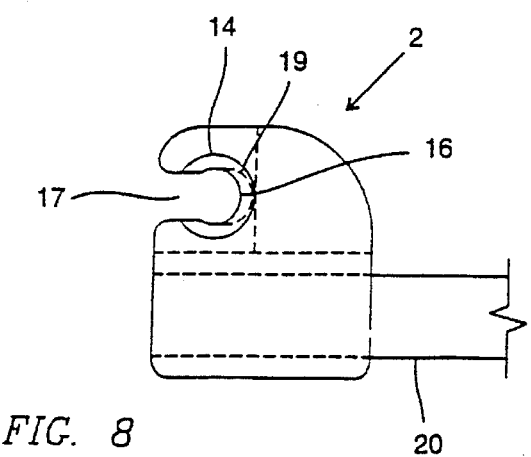
FIG. 8 Detailed buccal view of maxillary tube member.

Maxillary tube member unit 2 comprises a thin wall tube fitted with a specially modified spherical socket. The socket body is composed of any corrosion-resistant material suitable for oral use such as 300 series stainless steel, and can be produced by any of a number of manufacturing process including but not limited to: casting, sintering, machining, extruding/machining. The main form of the socket body comprises a tubular sleeve 10 with a flange 11 extending out of one side of the sleeve. As viewed from the end (FIG. 9), it can be seen that the flange is offset from the centerline of the tubular sleeve by approximately half the diameter of ball joint ball. This offset 12 in conjunction with the gently curving face 13 of the socket body will provide an appliance with a profile and tissue contact surfaces that will greatly minimize irritation of the oral tissues.

A hole 14 sunk into the face of the flange forms the basis for the ball socket. This hole is cylindrical with a hemispherical bottom 15 with said cylinder and hemi-sphere having a diameter of a few thousandths larger than the diameter of the ball of the joint attachments. This small clearance will facilitate a free moving fit of the ball and socket joint in the assembled appliance.

On the center axis of the previously mentioned cylindrical hole and hemisphere is a smaller cylindrical hole 16 which continues on through the flange. This cylindrical hole is somewhat larger than the stem 6 of the ball joint attachments, yet smaller than the ball diameter. A slot 17 in the side of the flange and parallel to the tubular sleeve intersects the socket at its distal quadrant. This slot 17 is sized to allow a clearance fit for the ball joint attachment stem which will pass through it in the assembly procedure to be detailed later.

From the top view (FIG. 2), it can be seen that the back of the flange behind the ball socket forms a dome-shaped profile 18. This feature provides clearance for the flange of the ball joint attachment as the ball socket swivels in the ball joint. An angled cutout 19 in the bottom of the aforementioned through hole extends the range of rotation of the ball socket assembly on the ball joint, thereby increasing the lateral freedom of movement of the complete appliance.

The above described socket body is assembled to a thin-wall tube to form the telescope tube unit. This assembly is performed by inserting the thin wall tube into the tubular sleeve of the socket body such that one end of the tube is flush with the end of the socket body with the stem clearance slot. The tube is then permanently affixed in this location by welding, soldering, or equivalent process. Note: The examples and diagrams used to describe this part is the design for the upper right attachment. The upper left attachment would be a mirror image duplicate of the design previously described.

The mandibular rod member comprises a rod which has fitted on one end, a head with a specially modified spherical ball socket. The head 21 of the rod member is constructed of any of a number of corrosion resistant materials known for use in orthodontic hardware such as 300 series stainless steel and can be produced by machining blanks or extrusions, casting, sintering, or equivalent manufacturing process.

Figure 5:
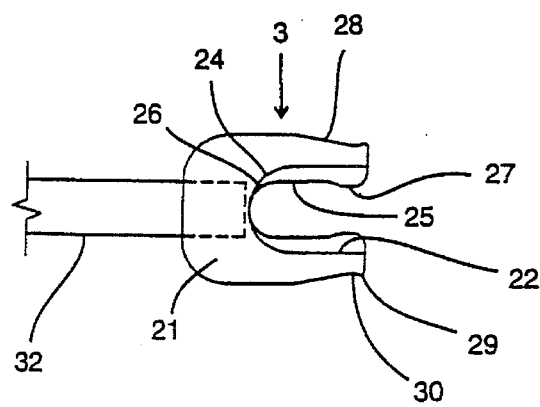
FIG. 5 Detailed view of mandibular rod member.
Figure 6:
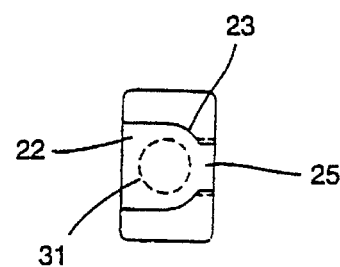
FIG. 6 Mesial view of FIG. 5.
Figure 7:
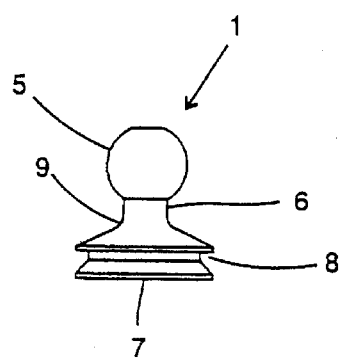
FIG. 7 Detailed view of ball hinge.
Figure 10:
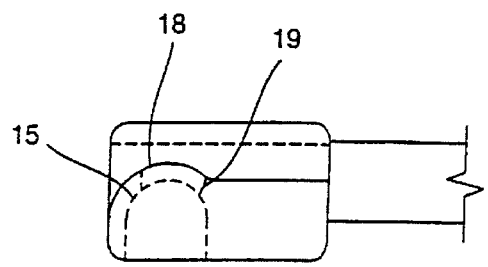
FIG. 10 Detailed gingival view of FIG. 8.

The head 21 possesses the general form of a U-shaped yoke with the slot of the U forming the socket for the ball and socket joint. A view of the cross-section (FIG. 6) indicates that the aforementioned slot is actually a compound shape formed by the intersection of two individual adjacent parallel slots. The top slot 22 is sized to be a clearance fit for the ball 5 of the ball joint and has a spherical bottom 23 and end 24 which have diameters equal to the slot width. The depth of this slot is approximately equal to the width and thus does not break through to the back of the socket head 21. The second slot 25 is parallel with the previously described slot and on the same centerline as viewed from the front (FIG. 5). This slot originates in the bottom of the top slot 22 and extends through to the back surface of the socket head, thus forming a slot completely through the part. This slot is sized to be a slight clearance fit around the stem 6 of the ball joint attachments. The walls of this slot are flat and square but the closed end of the slot terminates in a cylindrical radius 26 with a diameter equal to the width of the slot 25. Note that the narrow slot is as long as the wide slot; therefore, the center of the narrow slot terminating radius is farther from the slot opening than the center of the large slot terminating radius. This feature is important in allowing a wide angle of rotation of the assembled ball and socket joint located on each of the side walls of the small slot adjacent to the open end of the slot are two raised protrusions 27. These protrusions are sized to the opening of the slot a few thousandths smaller than the stems of the ball joint attachments. The function of these protrusions will be further described in discussions about implementation of the appliance.

The outside surfaces of the legs of the U-shape have a gentle taper 28 which reduces the width toward the open end of the slot. At the very ends of these surfaces, a protrusion juts out 29, and effectively forms an indent 30 at the intersection of the taper and protrusion. These indents and protrusions will aid in the proper seating of plier tips used in the installation of the appliances. The taper 28 on the sides of the legs aid in controlling the proper forming of legs when installed on the patient.

Centered on the back of the socket assembly head is a hole 31 which is axially aligned with the length of the slot. A rod 32 is fitted into this hole and attached by means of welding, soldering, pressing, or equivalent means. The resultant assembly is the completed mandibular rod member 3. Because of the symmetry of this unit, the same design is suitable for the left and right sides of the appliance.

Figure 11:
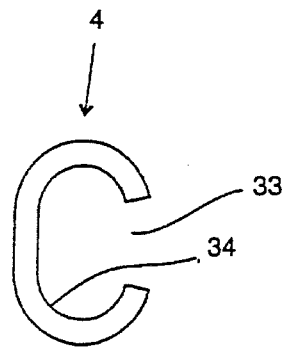
FIG. 11 Detailed end view of split spacer ring.

The appliance advancement spacers 4 (FIG. 11) are effectively short thin wall cylinders split longitudinally and spread open such that the cross-section of the cylinder has the general shape of a "C". The opening of the split 33 is approximately the diameter of the mandibular rod. The length of the arc 34 of the inside of the spacer is a few thousandths smaller than the circumference of the rod's outside diameter so that the spacer could be crimped fully closed onto the said rod. The spacer would be produced in a number of lengths according to typical adjustment increments used in current treatment therapies of this type.

All descriptions and explanations up to this point pertain to the components of this device as they are manufactured and supplied for use to the doctor. Following are descriptions of the application of the device in orthodontic treatment and explanation of the features provided by this design.

Ball joint attachments (1). In the implementation of this invention four ball joint attachments are attached to the dental arches of the patient and thus serve as the anchoring means for transmitting the forces from the appliance to the patient's dentition. The actual location and means used to secure the ball joint attachments to the patient's dentition is the same as any number of mandibular advancing devices currently known to the field including the Herbst device and is ultimately determined by the doctor's individual treatment philosophy and personal preference. The ball joint attachments would typically be located one each on the right and left molar of the maxillary arch with the base of the flange parallel and facing the buccal surface of the tooth. Another pair would be located one each on the right and left bicuspid of the mandibular arch with the base of the flange parallel and facing the labial surface of the tooth.

Typical techniques for applying the ball joint attachments include but are not limited to: welding and/or soldering to an orthodontic band; welding and/or soldering to dental crowns; welding and/or soldering to orthodontic structures; and attachment to a metal/acrylic splint-type device.

The initial step in the installation of the appliance to the patient is to install the chosen anchor appliance which is fitted with the ball joint attachments. This procedure is determined by the type of anchoring device employed and the personal techniques preferred by the practitioner. This procedure would be the same as it was for many of the known available appliances.

The next step is to attach the maxillary tube member to the maxillary ball joint attachment. This procedure is much simpler with this design than with currently available devices and the simple one piece design of the socket will make it more reliable. This member is applied by holding it in an orientation such that the socket hole in the flange is directly mesial of the ball and the tube is pointed generally in a buccal direction (FIG. 12). In this position, the socket can be freely engaged onto the ball joint (FIG. 13). While maintaining the socket engagement on the ball, the tube end of the member is rotated toward the mesial, (as the socket is rotated, the ball stem is engaged in the socket slot, ultimately rotating to the bottom of it). Until the tube member is oriented along side the buccal surface of the patient's maxillary arch (FIG. 14, 15, 16). When the maxillary member reaches the said position, the ball and socket joint are securely locked together, yet the member is free to rotate through a sufficient range of motion that the normal movement of the jaws will not be unduly inhibited by the appliance. In subsequent steps in the application of the appliance, the maxillary member will be limited to a range of orientation which will not allow the ball and socket hinge to disengage.

Figure 1:
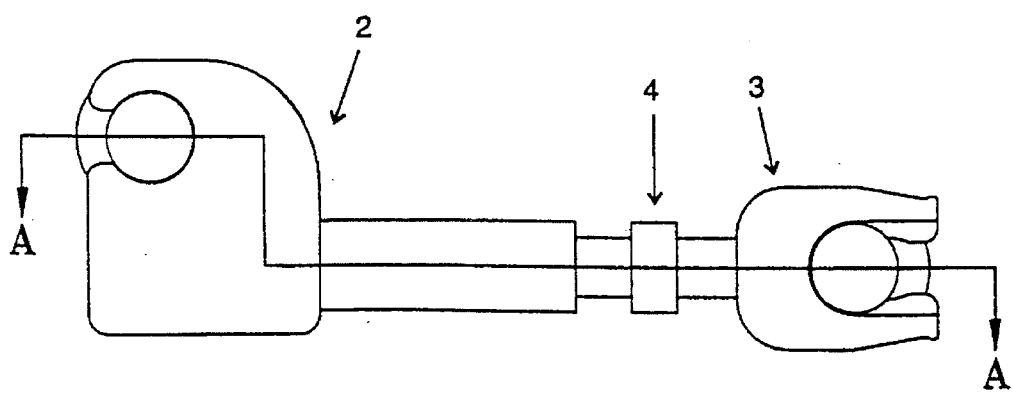
FIG. 1 Front view assembly of all components for right side.
Figure 17:
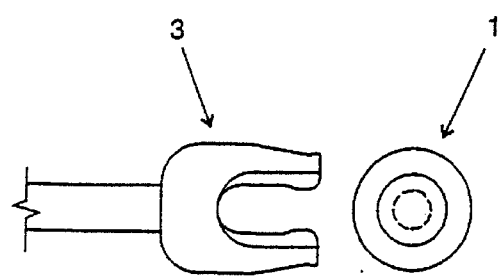
(FIG. 17 and 18 Assembly sequence of mandibular hinge.)
Figure 18:
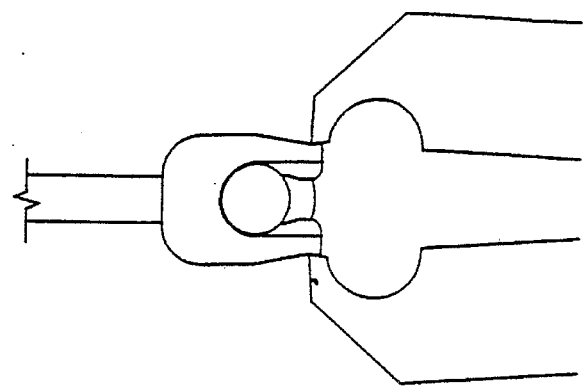

The next step in the installation of the device is the installation of the mandibular rod member. The rod end of the mandibular member is inserted into the tube of the maxillary member that was previously placed (FIG. 1). The assembly is then oriented such that the narrow slot of the socket is facing the teeth and the opening of the slot directly distal of the ball attachment (FIG. 17). From this position, the socket can be gently engaged onto the ball attachment. The two raised protrusions 27 on the inside of the slot will cause the socket to engage on the ball attachment with a light interference fit and will prevent the socket from disengaging until the subsequent step is complete. The final step of the arm installation is closing the front of the mandibular socket slot to lock it on the ball (FIG. 18). This is accomplished by locating pliers such that the jaws rest in the indent 30 on the socket legs and squeezing the legs shut. During the squeezing of the socket, the ball is tight in the socket, however, when it is released, the spring-back of the legs permit the proper clearance for free movement. This mode of assembly to the ball joint attachment is accomplished through plastic deformation of the mandibular socket legs; however, assembly could also be accomplished through elastic deformation alone by increasing the interference between the mandibular socket and ball joint attachment. The completed ball and socket assembly will permit free range of jaw motion in all desirable directions.

Figure 19:
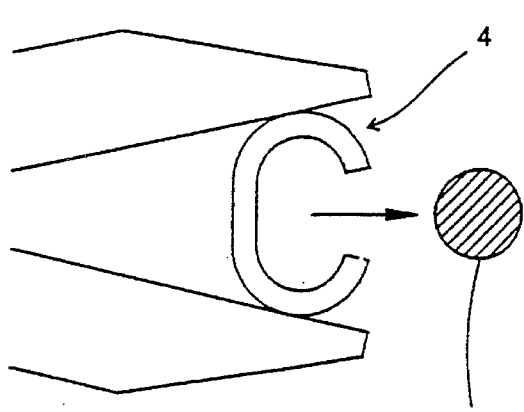
(FIG. 19 and 20 Assembly sequence of split spacer ring to mandibular rod member.)
Figure 20:
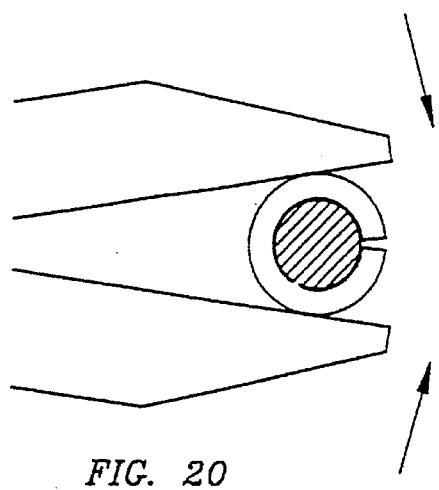
Figure 21:
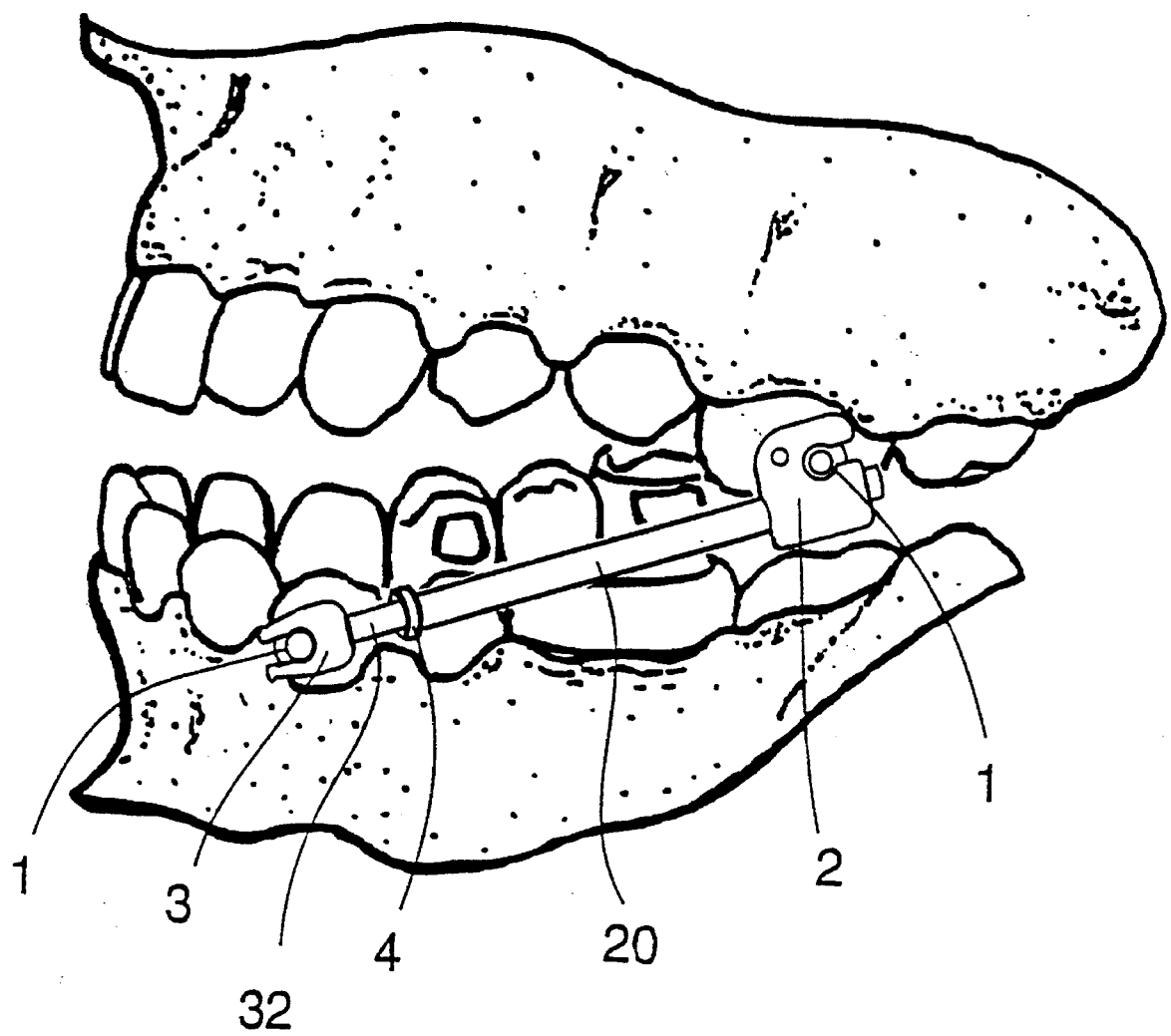
FIG. 21 shows the assembly installed on a patient.

The entire procedure described will be repeated for the other side of the patient's dental arch. During the course of treatment, the patient's mandible will advance and it becomes necessary to increase the effective length of the rod and tube assembly one or more times. In mandibular advancing device appliances currently known, it is necessary to disassemble at least one end of each assembly in order to facilitate this adjustment. The length adjustment procedure with the new invention is quickly and easily accomplished without disassembly of the rod and tube assembly. In this invention, the said lengthening process is accomplished with the use of the appliance advancement spacers 4 previously described with the patient's jaws slightly open, the mandibular rod member will be partially retracted from the maxillary tube member, exposing a length of the rod from the mandibular unit. An advancement spacer 4 held in a pair of pliers (FIG. 19) with the slot facing forward, can be slipped on the rod 32 and crimped in place (FIG. 20). The spacer placed in this manner will increase the length of the assembly in the closed position, thus increasing the active force on the mandible. The spacers will be available in a number of lengths and the doctor will select the spacer or combination of spacers to achieve the desired treatment results.

We claim:

1. In an orthodontic device for attachment to teeth of the upper and lower jaw of a patient for the purpose of moving teeth and/or stimulating mandibular jaw bone growth, comprising a pair of telescoping mechanisms, each having an opposite end portion, said telescoping mechanisms comprising a telescope outer tube portion and a telescope inner rod portion, said device comprising attachment means for securing each of the two opposite end portions to one or more teeth of the patient, the improvement comprising said attachment means including a ball and socket assembly, said ball having a sphere integrally connected to a stem terminating in a flange which is adapted to be affixed to the outer face of one or more teeth by an orthodontic device, said socket comprising a flange attached radially to said tube portion, the socket comprising a hemispherical shaped cavity intruding into a face of said flange, the diameter of said cavity being sized such that it provides a clearance fit around the sphere of said ball; a slot extending from the edge of said flange into the center of said hemispherical shaped cavity through to an opposite face of the flange, with said stem of said ball extending through said slot, whereby coupling of said flange to said ball is accomplished by pivoting said socket approximately 120 degrees about said ball.

2. In an orthodontic device for attachment to teeth of the upper and lower jaw of a patient for the purpose of moving teeth and/or stimulating mandibular jaw bone growth, comprising a pair of telescoping mechanisms, each having an opposite end portion, said telescoping mechanisms comprising a telescope outer tube portion and a telescope inner rod portion, said device having attachment means for securing each end portion to one or more teeth of the patient, the improvement comprising said attachment means including a ball and socket assembly, said ball having a sphere integrally connected to a stem terminating in a flange which is adapted to be affixed to the outer face of one or more teeth by an orthodontic device, said socket comprising a forked yoke attached longitudinally to the end portion of said rod portion, the socket including a hemispherical shaped cavity intruding into a face of said yoke and extending out through a front end of the yoke, the diameter of the cavity being sized such that it provides a clearance fit around the sphere of said ball, a slot extending into and intersecting with the cavity from an opposite face of said yoke, said stem of said ball extending through said slot, whereby coupling of said socket to said ball is accomplished by slight compressive deformation of said slot in said yoke around said ball, by utilizing suitable instruments.

* * * * *